United States Patent
Koguchi et al.

(10) Patent No.: US 12,133,935 B2
(45) Date of Patent: Nov. 5, 2024

(54) MEDICAL DEVICE

(71) Applicant: AGC Inc., Chiyoda-ku (JP)

(72) Inventors: Ryohei Koguchi, Chiyoda-ku (JP);
Hajime Eguchi, Chiyoda-ku (JP);
Kyoko Yamamoto, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 1162 days.

(21) Appl. No.: 16/918,072

(22) Filed: Jul. 1, 2020

(65) Prior Publication Data

US 2020/0330653 A1    Oct. 22, 2020

Related U.S. Application Data

(63) Continuation of application No. PCT/JP2019/007931, filed on Feb. 28, 2019.

(30) Foreign Application Priority Data

Apr. 10, 2018  (JP) .................. 2018-075271

(51) Int. Cl.
| | |
|---|---|
| *A61L 31/10* | (2006.01) |
| *A61L 31/02* | (2006.01) |
| *C08L 33/08* | (2006.01) |
| *C08L 33/14* | (2006.01) |
| *C09D 171/02* | (2006.01) |

(52) U.S. Cl.
CPC ............. *A61L 31/10* (2013.01); *A61L 31/026* (2013.01); *C08L 33/08* (2013.01); *C08L 33/14* (2013.01); *C09D 171/02* (2013.01); *A61L 2400/18* (2013.01)

(58) Field of Classification Search
CPC ..... C08F 230/08; C08G 65/336; C08G 63/66; C08G 63/668; C08G 63/672; C09D 171/02; C09D 133/08; C09D 133/14; C09D 167/025; C08L 67/025
See application file for complete search history.

(56) References Cited

U.S. PATENT DOCUMENTS

| | | | |
|---|---|---|---|
| 4,680,201 A | 7/1987 | Hjerten | |
| 2005/0240098 A1* | 10/2005 | Zhong | G01R 33/285 600/420 |
| 2006/0088666 A1* | 4/2006 | Kobrin | B82Y 30/00 427/255.6 |
| 2016/0083610 A1* | 3/2016 | Lin | C08F 226/02 526/279 |
| 2020/0299626 A1* | 9/2020 | Koguchi | C12Q 1/025 |
| 2020/0346972 A1* | 11/2020 | Eguchi | C09D 143/04 |

FOREIGN PATENT DOCUMENTS

| | | |
|---|---|---|
| JP | 2014-020938 A | 2/2014 |
| JP | 2018-070716 A | 5/2018 |

OTHER PUBLICATIONS

International Search Report issued Jun. 4, 2019 in PCT/JP2019/007931 filed on Feb. 28, 2019, 2 pages.

* cited by examiner

*Primary Examiner* — Kregg T Brooks
(74) *Attorney, Agent, or Firm* — Oblon, McClelland, Maier & Neustadt, L.L.P.

(57) ABSTRACT

To provide a medical device, whereby the non-specific absorption amount is reduced, its durability is excellent and eluents from the surface layer are reduced. The medical device comprises a device substrate and a surface layer provided on at least part of the surface of the device substrate in contact with water, wherein at least part of the surface of the device substrate is made of an inorganic material, the surface layer is made of a cured product of a compound having a biocompatible group and an alkoxysilyl group, the content of the biocompatible group in the compound is from 25 to 83% by mass, and the content of the alkoxysilyl group is from 2 to 70% by mass.

8 Claims, No Drawings

MEDICAL DEVICE

TECHNICAL FIELD

The present invention relates to a medical device.

BACKGROUND ART

Heretofore, as a method for analyzing a biological substance, a method of using a biochip has been known. In this method, molecules to capture a specific biological substance (protein or the like) are fixed on the chip surface, and the biological substance captured by the molecules is detected.

However, in the biochip, if non-specific proteins other than the biological substance to be detected will be adsorbed to portions where the molecules to capture the biological substance are not fixed, there will be a problem that such non-specific proteins become a noise at the time of detection, to deteriorate the detection accuracy.

Therefore, as a method for reducing the adsorption amount of non-specific proteins (non-specific adsorption amount), a method for forming a cured material layer made of a copolymer of 2-methacryloyloxyethylphosphorylcholine (MPC) and n-butyl methacrylate (BMA) on the substrate (see, for example, Patent Document 1), or a method for forming a cured layer by coating the substrate surface with a silane coupling agent and then radically polymerizing it with acrylamide (see, for example, Patent Document 2) has been proposed.

However, in the above-mentioned conventional method, there has been a problem such that when the biochip is used for a long period of time, the non-specific adsorption amount tends to be increased, or components of the cured layer tend to be eluted, to deteriorate the detection accuracy.

PRIOR ART DOCUMENTS

Patent Documents

Patent Document 1: JP-A-2014-20938
Patent Document 2: U.S. Pat. No. 4,680,201

DISCLOSURE OF INVENTION

Technical Problem

It is the object of the present invention to provide a medical device, whereby the non-specific adsorption amount of cells, proteins, etc. (non-specific adsorption amount) is reduced, its durability is excellent, and the amount of eluents from the surface layer is reduced.

Solution to Problem

The medical device of the present invention is a medical device comprising a device substrate and a surface layer disposed on at least part of the surface of the device substrate in contact with water, wherein at least part of the surface on which the surface layer is provided on the device substrate is made of an inorganic material, the surface layer is made of a cured product of a compound having a biocompatible group and an alkoxysilyl group, and the biocompatible group is made of at least one type selected from the group consisting of a structure represented by the following formula 1, a structure represented by the following formula 2 and a structure represented by the following formula 3, the content of the biocompatible group in the compound is from 25 to 83% by mass, and the content of the alkoxysilyl group is from 2 to 70% by mass,

Formula 1

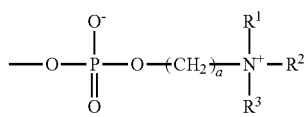

Formula 2

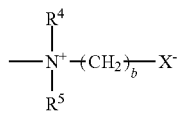

Formula 3 provided that in the formula 1, n is an integer of from 1 to 300, and from 50 to 100 mol % in the structure represented by the formula 1 is a structure represented by the formula 1 in a structure represented by the following formula 4, n in the formula 4 is an integer of from 1 to 300, and $R^6$ is a hydrogen atom or a $C_{1-5}$ alkyl group, in the formula 2, $R^1$ to $R^3$ are each independently a 01-5 alkyl group, and a is an integer of from 1 to 5, in the formula 3, $R^4$ and $R^5$ are each independently a $C_{1-5}$ alkyl group, $X^-$ is a group represented by the following formula 3-1 or a group represented by the following formula 3-2, and b is an integer of from 1 to 5,

Formula 4

Formula 3-1

Formula 3-2

In the medical device of the present invention, when the surface layer is immersed in water at 40° C. for 7 days, the elution amount of total organic carbon (TOC) per unit area of 1 cm² of the surface layer is preferably at most 10 mg/L.

In the medical device of the present invention, the above compound is preferably such a compound that in a polyoxyethylene polyol or a polyoxyethylene alkyl ether having at least one hydroxy group (wherein the alkyl has from 1 to 5 carbon atoms), an alkoxysilyl group is introduced via a hydroxy group and a linking group which the polyoxyethylene polyol or the polyoxyethylene alkyl ether has.

In the medical device of the present invention, the above compound is preferably such a compound that in a polyoxyethylene polyol or a polyoxyethylene polyol alkyl ether having at least one hydroxy group (wherein the alkyl has from 1 to 5 carbon atoms), an alkoxysilyl group is introduced so as to be bonded via an oxygen atom derived from the hydroxy group, or via a linking group having an oxygen atom derived from the hydroxy group bonded to $-(CH_2)_k-$, $-CONH(CH_2)_k-$, $-(CF_2)_k-$, $-CO(CH_2)_k-$, $-CH_2CH(-OH)CH_2O(CH_2)_k-$ (k represents an integer of from 2 to 4), $-CH_2OC_3H_6-$, or $-CF_2OC_3H_6-$.

In the medical device of the present invention, the above compound is preferably a copolymer having units based on a (meth)acrylate having a structure represented by the above formula 1 (provided that from 50 to 100 mol % is the structure represented by the formula 1 in the structure represented by the above formula 4), and units based on a (meth)acrylate having an alkoxysilyl group.

In the medical device of the present invention, the above compound is preferably a copolymer having units based on a (meth)acrylate having a structure represented by the above formula 1 (provided that from 50 to 100 mol % is the structure represented by the formula 1 in the structure represented by the above formula 4), units based on a (meth)acrylate having an alkoxysilyl group, and units represented by the formula (B12):

Formula (B12)

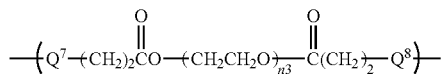

provided that in the formula (B12), $Q^7$ and $Q^8$ are each independently a divalent organic group, and n3 is an integer of from 20 to 200.

In the medical device of the present invention, the above compound preferably comprises a copolymer having units based on a (meth)acrylate having a structure represented by the above formula 1 and units based on a (meth)acrylate having an alkoxysilyl group, and a polymer consisting only of units based on a (meth)acrylate having a structure represented by the above formula 1, and from 50 to 100 mol % in the structure represented by the above formula 1 contained in the solid content of the above compound has a structure represented the formula 1 in the structure represented by the above formula 4.

In the medical device of the present invention, the above compound is preferably a copolymer having units represented by the following formula (A), units represented by the following formula (B11) and units represented by the following formula (B12), Formula (A)

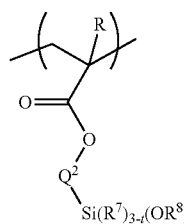

Formula (B11)

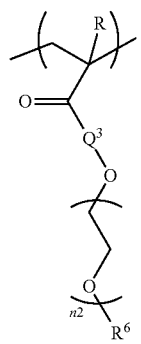

-continued

Formula (B12)

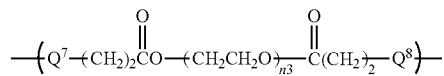

provided that the symbols in the formula (A), the formula (B11) and the formula (B12) are as follows;

in the formula (A) and the formula (B11), R is a hydrogen atom or a methyl group;

in the formula (A), $Q^2$ is a divalent organic group, $R^7$ and $R^8$ are each independently a $C_{1-18}$ alkyl group, t is an integer of from 1 to 3, and when $R^7$ and $OR^8$ are present in a plurality, the respective $R^7$ and $R^8$ may be the same or different;

in the formula (B11), $Q^3$ is a single bond or a divalent organic group, n2 is an integer of from 1 to 300, and $R^6$ is a hydrogen atom or a $C_{1-5}$ alkyl group;

in the formula (B12), $Q^7$ and $Q^8$ are each independently a divalent organic group, and n3 is an integer of from 20 to 200.

$Q^7$ and $Q^8$ are preferably —C(CH$_3$)(COOC$_2$H$_5$)—, —C(CH$_3$)(COOCH$_3$)— or —C(CH$_3$)(CN)—, more preferably —C(CH$_3$) (COOCH$_3$)— or —C(CH$_3$)(CN)—, and from the viewpoint of easy availability and ease of production at the time of polymerization, further preferably —C(CH$_3$)(CN)—.

In the medical device of the present invention, the device substrate is preferably made of glass.

Advantageous Effects of Invention

According to the present invention, it is possible to provide a medical device whereby the non-specific adsorption amount is reduced, its durability is excellent, and the amount of eluents from the surface layer is reduced.

DESCRIPTION OF EMBODIMENTS

Embodiments of the present invention will be described below. The present invention is not limited to the following description. Other embodiments may be included in the scope of the present invention as long as they match the spirit of the present invention. Further, embodiments in which the following embodiments and modified examples are optionally combined are also preferred examples.

In the present specification, a compound or group represented by a formula is also referred to as a compound or group with the number of the formula, and, for example, a compound represented by the formula 1 is also referred to as a compound 1.

In the present specification, a numerical range includes the upper limit value and the lower limit value of the range.

A "(meth)acrylate" is a general term for an acrylate and a methacrylate.

A "unit" in the copolymer means a portion derived from the monomer, formed by polymerization of the monomer.

A "biocompatible group" means a group having a nature to prevent a protein or cells, etc. from sticking to the surface of the material and becoming activation.

The medical device of the present invention comprises a device substrate and a surface layer, and the surface layer is disposed on at least part of the surface of the device substrate in contact with water. And, the surface layer is a cured product of a compound (hereinafter referred to as a "compound (X)") which is a compound having a biocompatible group made of at least one type selected from the group consisting of the structure represented by the above formula 1, the structure represented by the above formula 2, and the structure represented by the above formula 3, and an alkoxysilyl group, wherein the content the biocompatible group is from 25 to 83% by mass and the content of the alkoxysilyl group is from 2 to 70% by mass.

The solid content in the compound means the residual content obtained by vacuum-drying the compound at 80° C. for 3 hours and removing volatile components. Further, in the following description, unless otherwise specified, the "biocompatible group" is a group made of at least one type selected from the group consisting of the structure represented by the above formula 1, the structure represented by the above formula 2, and the structure represented by the above formula 3.

The medical device of the present invention has a surface layer made of the cured product of the compound (X) on the surface of the medical device substrate in contact with water, whereby the non-specific adsorption amount can be reduced, and the effect thereof can be sustained.

It is considered that since the compound (X) has a sufficient amount of the biocompatible group, the obtained cured product also has a sufficient amount of the biocompatible group, and since the biocompatible group contains water, the non-specific adsorption amount is effectively reduced. Further, it is considered that since the compound (X) has a predetermined amount of the alkoxysilyl group, the alkoxysilyl group is firmly bonded to the surface of the device substrate at the time when the compound (X) is cured, so that the effect of reducing the non-specific adsorption amount will be sustained.

Here, since the compound (X) has an alkoxysilyl group, it undergoes a hydrolysis reaction to form a silanol group (Si—OH). Then, the silanol groups undergo a dehydration condensation reaction to form a siloxane bond (Si—O—Si) thereby to form a cured product. Since the siloxane bond can form a three-dimensional matrix structure, it is considered that elution from the surface layer can be suppressed.

In a case where the compound (X) is cured on the surface of the device substrate, the silanol group generated by the hydrolysis reaction of the compound (X) forms, at the same time as forming the above Si—O—Si bond, a chemical bond (substrate-O—Si) by a dehydration condensation reaction with a hydroxy group (substrate-OH) on the surface of the device substrate. As a result, the obtainable surface layer firmly adheres to the surface of the device substrate, and thus has high durability, for example, water resistance.

As a constituent material for the device substrate, an inorganic material usually used for medical devices can be used without particular limitation. Specifically, the inorganic material may be a metal, glass, and a composite material of two or more types of them, and it may be suitably selected depending upon the application. In the medical device of the present invention, the constituent material for the device substrate is preferably a material having a hydroxy group on the surface of a molded body made of the material, from the viewpoint of adhesion to the surface layer, and glass is suitable. Further, when the surface of the device substrate does not have a hydroxy group, it is preferred to introduce a hydroxy group by a known method, for example, a physical treatment method such as corona treatment or a chemical treatment method such as primer treatment. Further, the device substrate does not need to be formed entirely of the above material as long as at least part or the entire surface on which the surface layer is to be provided is formed of the above material.

The surface layer is composed of a cured product of the compound (X). The compound (X) has a biocompatible group made of at least one type selected from the group consisting of the structure represented by the formula 1, the structure represented by the formula 2 and the structure represented by the formula 3, and an alkoxysilyl group.

The compound (X) contains the biocompatible group in a proportion of from 25 to 83% by mass and the alkoxysilyl group in a proportion of from 2 to 70% by mass.

$$—O—(CH_2CH_2O)_{n}—$$ Formula 1

$$—O—\underset{\underset{O}{\|}}{\overset{\overset{O^-}{|}}{P}}—O—(CH_2)_{a}—\underset{\underset{R^3}{|}}{\overset{\overset{R^1}{|}}{N^+}}—R^2$$ Formula 2

$$—\underset{\underset{R^5}{|}}{\overset{\overset{R^4}{|}}{N^+}}—(CH_2)_{b}—X^-$$ Formula 3

Here, in the formula 1, n is an integer of from 1 to 300, and from 50 to 100 mol % in the structure represented by the formula 1 is the structure represented by the formula 1 in the structure represented by the following formula 4. In the formula 4, n is an integer of from 1 to 300, and $R^6$ is a hydrogen atom or a $C_{1-5}$ alkyl group.

In the formula 2, $R^1$ to $R^3$ are each independently a $C_{1-5}$ alkyl group, and a is an integer of from 1 to 5.

In the formula 3, $R^4$ and $R^5$ are each independently a $C_{1-5}$ alkyl group, and $X^-$ is a group represented by the following formula 3-1 or a group represented by the following formula 3-2, and b is an integer from 1 to 5.

$$—O—(CH_2CH_2O)_{n}—R^6$$ Formula 4

$$\underset{O}{\overset{\diagdown}{C}}{\diagup}^{O^-}$$ Formula 3-1

$$\underset{O}{\overset{\diagdown}{\underset{\|}{S}}}{\overset{\diagup O^-}{\|}}_{O}$$ Formula 3-2

In the present specification, the alkyl group may be any of linear, branched and cyclic, or may be a combination thereof.

The biocompatible group which the compound (X) has, is made of at least one type selected from the structure 1 (wherein from 50 to 100 mol % is the structure 1 in the structure 4), the structure 2 and the structure 3. Hereinafter, the structure 1 (wherein from 50 to 100 mol % is the structure 1 in the structure 4) will be referred to as the "structure 1 (4)". The biocompatible group may be composed of only one type of the structure 1 (4), the structure 2 and the structure 3, or may be composed of two or more types. The structure 1 (4) is preferred as the biocompatible group.

The alkoxysilyl group which the compound (X) has, may, for example, be a group represented by the formula 5.

$$—Si(R^7)_{3-t}(OR^8)_{t}$$ Formula 5

Here, in the formula 5, $R^7$ is a $C_{1-18}$ alkyl group, $R^8$ is a $C_{1-18}$ alkyl group, and t is an integer of from 1 to 3. In a case where $R^7$ and $OR^8$ are present in a plurality, the respective $R^7$ and $R^8$ may be the same or different. From the viewpoint of production, they are preferably the same.

From the viewpoint of adhesion between the device substrate and the surface layer, t is preferably at least 2, more preferably 3. From the viewpoint of steric hindrance at the time of the condensation reaction, $R^7$ is preferably a $C_{1-6}$ alkyl group, more preferably a methyl group or an ethyl group. From the viewpoint of the hydrolysis reaction rate and the volatility of by-products at the time of the hydrolysis reaction, $R^8$ is preferably a $C_{1-6}$ alkyl group, more preferably a methyl group or an ethyl group.

The compound (X) may, for example, be a compound (X1) having a polyoxyethylene chain as a main chain and having an alkoxysilyl group at a terminal or a side chain, a compound (X2) having a hydrocarbon chain formed by polymerization of an ethylenic double bond as a main chain, and a biocompatible group and an alkoxysilyl group at a side chain, or a compound (X3) containing both a hydrocarbon chain formed by polymerization of an ethylenic double bond and a polyoxyethylene chain, as a main chain and having a biocompatible moiety and an alkoxysilyl group at a side chain, which satisfies the requirements as the compound (X).

The compound (X1) is obtainable, for example, by introducing to a polyoxyethylene polyol or a polyoxyethylene alkyl ether having at least one hydroxy group (wherein the alkyl has from 1 to 5 carbon atoms), an alkoxysilyl group via the hydroxy group and a linking group which the above polyoxyethylene polyol or the above polyoxyethylene alkyl ether has. More specifically, the compound (X1) is obtainable, for example, by reacting to a polyoxyalkylene polyol containing a polyoxyethylene chain or a polyoxyalkylene alkyl ether containing a polyoxyethylene chain and having at least one hydroxy group (wherein the alkyl has from 1 to 5 carbon atoms), a silane compound having a group reactive with the hydroxy group and an alkoxysilyl group (hereinafter referred to also as a silane compound (S)), at a predetermined ratio.

The polyoxyalkylene polyol to be used, may be a compound obtainable by ring-opening addition polymerization of an alkylene monoepoxide containing at least ethylene oxide to a polyol having a relatively low molecular weight such as an alkane polyol, an etheric oxygen atom-containing polyol or a sugar alcohol. The oxyalkylene group in the polyoxyalkylene polyol may be an oxyethylene group, an oxypropylene group, an oxy-1,2-butylene group, an oxy-2,3-butylene group, an oxyisobutylene group, or the like.

The polyoxyalkylene alkyl ether to be used, may be a compound in which part of the hydroxy groups of such a polyoxyalkylene polyol is ether-bonded with a $C_{1-5}$ aliphatic alcohol. In the following description, unless otherwise specified, a "polyoxyalkylene alkyl ether" refers to a polyoxyalkylene alkyl ether having at least one hydroxy group (provided that the alkyl has from 1 to 5 carbon atoms). The same applies when "oxyalkylene" is changed to "oxyethylene".

The oxyalkylene group which the polyoxyalkylene polyol and the polyoxyalkylene alkyl ether has, may be composed solely of an oxyethylene group, or may be composed of a combination of an oxyethylene group and another oxyalkylene group. From the viewpoint of easy molecular design as the compound (X1), the polyoxyethylene polyol or the polyoxyethylene alkyl ether having only an oxyethylene group is preferred. Hereinafter, the polyoxyethylene polyol and the polyoxyethylene alkyl ether may be collectively referred to as a polyoxyethylene polyol or the like.

That is, the compound (X1) is preferably a reaction product of a polyoxyethylene polyol or the like and a silane compound (S). The number of hydroxy groups in the polyoxyethylene polyol or the like may be from 1 to 6, preferably from 1 to 4, particularly preferably from 1 to 3, from the viewpoint of easy molecular design as the compound (X1). Specifically, the polyoxyethylene polyol or the like, may be polyoxyethylene glycol, polyoxyethylene glyceryl ether, trimethylolpropane trioxyethylene ether, pentaerythritol polyoxyethylene ether, dipentaerythritol polyoxyethylene ether, a polyoxyethylene glycol monoalkyl ether (wherein the alkyl has from 1 to 5 carbon atoms), or the like.

For example, in a case where the polyoxyethylene polyol or the like is a polyoxyethylene glycol having 2 hydroxy groups, the compound (X1) may be a compound (X11) represented by the symbol (X11) in the formula, which is obtainable by reacting a polyoxyethylene glycol and a silane compound (S1) represented by $R^9\text{-}Q^{11}\text{-}Si(R^7)_{3-t}(OR^8)_t$.

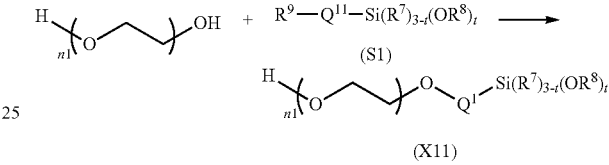

In the above reaction formula, n1 in the polyoxyethylene glycol is an integer of from 1 to 300, preferably from 2 to 100, more preferably from 4 to 20. $R^7$, $R^8$ and t in the silane compound (S1) are the same as in the case of the above formula 5, including the preferred embodiments. $R^9$ in the silane compound (S1) is a group reactive with a hydroxy group, and may be a hydroxy group, a carboxy group, an isocyanate group or an epoxy group. $Q^{11}$ is a $C_{2-20}$ divalent hydrocarbon group which may have an etheric oxygen atom between carbon-carbon atoms wherein a hydrogen atom may be substituted by a halogen atom such as a chlorine atom or a fluorine atom, or a hydroxy group. In a case where a hydrogen atom is to be substituted by a hydroxy group, the number of hydroxy groups to be substituted is preferably from 1 to 5.

In the formula (X11), $Q^1$ is a residue obtained by reacting $R^9\text{-}Q^{11}$ of the silane compound (Si) with the hydroxy group of the polyoxyethylene glycol, and may be represented by $R^{9'}\text{-}Q^{11}$ (the side bonded to O is $R^{9'}$ and the side bonded to the alkoxysilyl group is $Q^{11}$). $R^{9'}$ may be a single bond, —C(=O)—, —C(=O)NH—, —C(=O)N(CH$_3$)—, —C(=O)N(C$_6$H$_5$)— or —CH$_2$CH(—OH)CH$_2$O— corresponding to $R^9$. Hereinafter, —C(=O)N . . . will be shown as —CON . . . . For example, —C(=O)NH— will be shown as —CONH—.

$Q^1$ is preferably —(CH$_2$)$_k$—, —CONH(CH$_2$)$_k$—, —(CF$_2$)$_k$— (k represents an integer of from 2 to 4), —CH$_2$OC$_3$H$_6$—, —CF$_2$OC$_3$H$_6$—, etc. Among them, any one selected from —CONHC$_3$H$_6$—, —CONHC$_2$H$_4$—, —CH$_2$OC$_3$H$_6$—, —CF$_2$OC$_3$H$_6$—, —C$_2$H$_4$—, —C$_3$H$_6$— and —C$_2$F$_4$— is more preferred, and —CONHC$_3$H$_6$—, —CONHC$_2$H$_4$—, —C$_2$H$_4$— or —C$_3$H$_6$— is further preferred.

Further, the compound (X11) may be obtained by reacting polyoxyethylene glycol with allyl chloride under a basic condition and then silane-modifying it by a hydrosilylation reaction.

In the structure 1 in the compound (X11), the proportion of the structure 1 in the structure 4 is 100 mol %. That is, all of the structure 1 in the compound (X11) is the structure 1 in the structure 4. Namely, the oxyethylene chain in the compound (X11) preferably has a large proportion where one terminal is $R^6$. The content of the biocompatible group in the compound (X11) is the mass % of —$_{n1}$(OCH$_2$CH$_2$)—O— in the formula (X11), and the content of the alkoxysilyl group is the mass % of —Si(R$^7$)$_{3-t}$(OR$^8$)$_t$ in the formula (X11). The contents of the biocompatible group and the alkoxysilyl group in the compound (X11) are optionally adjusted depending upon the solid content composition of the composition (Y). For example, the content of the biocompatible group in the compound (X11) is preferably from 10 to 90% by mass, more preferably from 25 to 83% by mass, further preferably from 40 to 83% by mass, particularly preferably from 60 to 83% by mass. The content of the alkoxysilyl group in the compound (X11) is preferably from 1 to 70% by mass, more preferably from 2 to 70% by mass, further preferably from 2 to 45% by mass, particularly preferably from 10 to 30% by mass.

Further, a compound in which the terminal hydrogen atom in the compound (X11) is substituted by $R^6$ other than a hydrogen atom can also be used as a compound (X1). That is, in the above reaction formula, a compound obtainable by using a polyoxyethylene glycol monoalkyl ether (where the alkyl is $R^6$) instead of a polyoxyethylene glycol having 2 hydroxyl groups can also be used as a compound (X1). In that case, $R^6$ is preferably a methyl group or an ethyl group, more preferably a methyl group.

For example, in a case where the polyoxyethylene polyol is a polyoxyethylene glyceryl ether having 3 hydroxy groups, the compound (X1) may be a compound (X12) represented by the symbol (X12) in the following formula, which is obtained by reacting a polyoxyethylene glyceryl ether and a silane compound (S1) represented by $R^9$-$Q^{11}$—Si(R$^7$)$_{3-t}$(OR$^8$)$_t$ as shown by the following formula.

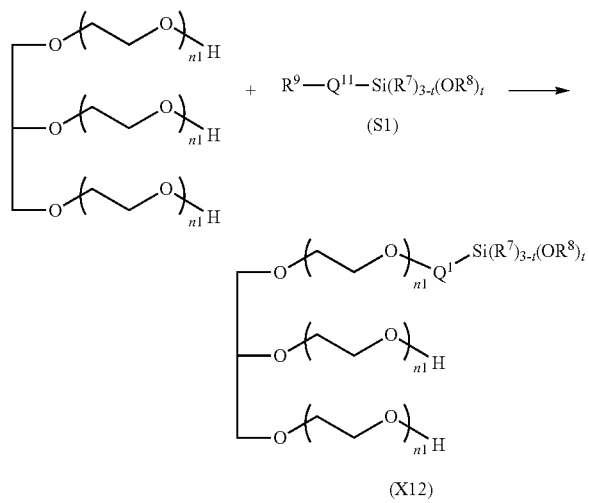

(X12)

In the above reaction formula, n1 in the polyoxyethylene glyceryl ether can be made to be the same as n1 in the polyoxyethylene glycol including preferred embodiments. The silane compound (Si) can be made to be the same as above. In the compound (X12), $Q^1$ can be made to be the same as $Q^1$ in the compound (X11) including preferred embodiments.

In the structure 1 in the compound (X12), the proportion of the structure 1 in the structure 4 is 67 mol %. The contents of the biocompatible group and the alkoxysilyl group in the compound (X12) can be made to be the same as in the compound (X11) including preferred embodiments.

Further, a compound in which the terminal hydrogen atom of O—(CH$_2$CH$_2$O)$_{n1}$—H in compound (X12) is substituted by $R^6$ other than a hydrogen atom can also be used as a compound (X1). In that case, $R^6$ is preferably a methyl group.

In the compound (X1), the content of the structure other than the biocompatible group and the alkoxysilyl group is preferably from 10 to 50% by mass, more preferably from 20 to 30% by mass from the viewpoint of achieving both reduction of the non-specific adsorption amount and water resistance. The weight average molecular weight of the compound (X1) is preferably from 100 to 10,000, more preferably from 500 to 2,000 from the viewpoint of easy availability of raw materials. The weight average molecular weight (hereinafter sometimes referred to as "Mw") of the compound (X1) is calculated by size exclusion chromatography.

In the foregoing, the compound (X1) has been described by taking polyoxyethylene glycol and polyoxyethylene glyceryl ether as examples of the polyoxyethylene polyol or the like. Similarly, with respect to a polyoxyethylene polyol or the like other than these, it is possible to produce the compound (X1) by suitably adjusting the proportion where the structure 1 is the structure 1 in the structure 4, the content of the biocompatible group, the content of the alkoxysilyl group, etc. to desired proportions.

The compound (X1) may further be a partially hydrolyzed condensate thereof. In a case where the compound (X1) is made to be a partially hydrolyzed condensate, the degree of condensation is suitably adjusted to bring the viscosity to a level not to bring about a trouble at the time of forming the surface layer on the surface of the device substrate as described below. From such a viewpoint of the viscosity, Mw of the partially hydrolyzed condensate is preferably from 1,000 to 1,000,000, more preferably from 1,000 to 100,000. The preferred range of Mw is the same for the following partially hydrolyzed co-condensate. The content (% by mass) of the alkoxysilyl group in the partially hydrolyzed condensate is treated to be equal to the content (% by mass) of the alkoxysilyl group in the silane compound as raw material. In the partially hydrolyzed co-condensate, the content (% by mass) of the alkoxysilyl group can be calculated from the mixing proportion of the silane compound as raw material.

The compound (X1) may be a partially hydrolyzed co-condensate obtained by partially hydrolyzing and co-condensing two or more compounds (X1) so as to contain a biocompatible group and an alkoxysilyl group in a desired ratio. The compound (X1) may further be a partially hydrolyzed co-condensate obtained by partially hydrolyzing and co-condensing a compound (X1) and an alkoxysilane compound having no biocompatible group so that the obtainable partially hydrolyzed condensate contains a biocompatible group and an alkoxysilyl group at a desired ratio as the compound (X).

The alkoxysilane compound having no biocompatible group may be an alkoxysilane compound represented by the following formula 6.

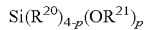    Formula 6

Here, in the formula 6, $R^{20}$ is a monovalent organic group having no polyoxyethylene chain, $R^{21}$ is a $C_{1-18}$ alkyl group, and p is an integer of from 1 to 4. In a case where $R^{20}$ and $OR^{21}$ are present in a plurality, the respective $R^{20}$ and $R^{21}$ may be the same or different. From the viewpoint of production, they are preferably the same.

Specifically, $R^{20}$ may be a $C_{1-18}$ alkyl group, and from the viewpoint of steric hindrance at the time of the condensation reaction, a methyl group is preferred.

From the viewpoint of the adhesion between the device substrate and the surface layer, p is preferably at least 2, more preferably 3 or 4, particularly preferably 4. From the viewpoint of the hydrolysis reaction rate and the volatility of by-products at the time of the hydrolysis reaction, $R^{21}$ is preferably a $C_{1-6}$ alkyl group, more preferably a methyl group or an ethyl group.

The compound (X2) may, for example, be a (meth) acrylate copolymer obtained by copolymerizing monomers comprising a (meth)acrylate having a biocompatible group and a (meth)acrylate having an alkoxysilyl group to be essential, and optionally other (meth)acrylates other than these. In this case, as the raw material monomers, the contents of the above respective (meth)acrylates are adjusted so that the obtainable (meth)acrylate copolymer contains a biocompatible group and an alkoxysilyl group in a desired ratio as the compound (X).

In other words, the compound (X2) is preferably a copolymer which contains units based on a (meth)acrylate having a biocompatible moiety and units based on a (meth)acrylate having an alkoxysilyl group at a predetermined ratio and optionally contains units based on other (meth)acrylates other than these.

Units based on a (meth)acrylate having a biocompatible moiety are meant for at least one type selected from units based on a (meth)acrylate having the structure 1, units based on a (meth)acrylate having the structure 2, and units based on a (meth)acrylate having the structure 3. Such units may specifically be units based on a (meth)acrylate having the structure 1 in a side chain (hereinafter referred to as units (B1)), units based on a (meth)acrylate having the structure 2 represented by the following formula (B2) and units based on a (meth)acrylate having the structure 3 represented by the following formula (B3). As units (B1), units based on a (meth)acrylate having the structure 4 represented by the following formula (B11) is preferred.

In the foregoing, units (B1) are units based on a (meth) acrylate having the structure 1. Units (B1) preferably contain units (B11) in an amount of from 50 to 100 mol %. That is, units (B1) may include units other than units (B11) in a proportion of at most 50 mol %. Units other than units (B11) may be units having a group other than $R^6$ in units (B11) instead of $R^6$, for example, units having a carbonyl group derived from a bifunctional (meth)acrylate. The proportion of units (B11) in units (B1) is preferably from 75 to 100 mol %, and it is particularly preferred that all (100 mol %) are units (B11). Hereinafter, the monomer to be a base for units (B1) will be referred to as a (meth)acrylate (B1).

Units (B1), units (B2) and units (B3) will be collectively referred to as units (B). Further, units based on a (meth) acrylate having an alkoxysilyl group may be units based on a (meth)acrylate represented by the following formula (A). Furthermore, units based on other (meth)acrylates may be units based on a (meth)acrylate represented by the following formula (C).

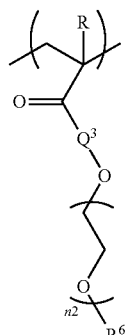

Formula (B11)

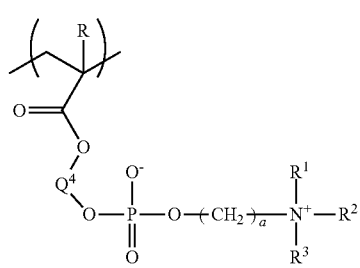

Formula (B2)

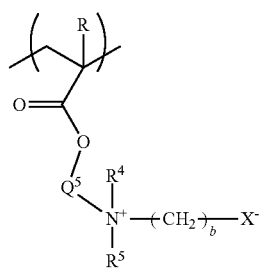

Formula (B3)

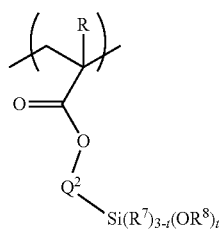

Formula (A)

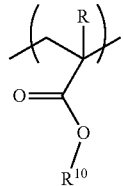

Formula (C)

Here, the symbols in the formula (B11), the formula (B2), the formula (B3), the formula (A) and the formula (C) are as follows.

In the formula (B11), the formula (B2), the formula (B3), the formula (A) and the formula (C), R is a hydrogen atom or a methyl group.

In the formula (B11), $Q^3$ is a single bond or a divalent organic group, n2 is an integer of from 1 to 300, and $R^6$ is a hydrogen atom or a $C_{1-5}$ alkyl group. n2 is preferably from 1 to 100, more preferably from 1 to 20.

In the formula (B2), $Q^4$ is a divalent organic group, $R^1$ to $R^3$ are each independently a $C_{1-5}$ alkyl group, and a is an integer of from 1 to 5.

In the formula (B3), $Q^5$ is a divalent organic group, $R^4$ and $R^5$ are each independently a $C_{1-5}$ alkyl group, and $X^-$ is group 3-1 or group 3-2, and b is an integer of from 1 to 5.

In the formula (A), $Q^2$ is a divalent organic group, $R^7$ and $R^8$ are each independently a $C_{1-18}$ alkyl group, t is an integer of from 1 to 3, and in a case where $R^7$ and $OR^8$ are present in a plurality, the respective $R^7$ and $R^8$ may be the same or different. Preferred embodiments of $R^7$, $R^8$ and t are the same as in the case of the above formula 5.

In the formula (C), $R^{10}$ is a hydrogen atom or a monovalent organic group having no biocompatible moiety and no alkoxysilyl group. $R^{10}$ is preferably a hydrogen atom or a $C_{1-100}$ alkyl group, more preferably a $C_{1-20}$ alkyl group.

$Q^2$, $Q^4$ and $Q^5$ are preferably a $C_{2-10}$ divalent hydrocarbon group which may have an etheric oxygen atom between carbon-carbon atoms, wherein a hydrogen atom may be substituted by a halogen atom such as a chlorine atom or a fluorine atom, or a hydroxy group.

$Q^2$ is preferably —$C_2H_4$—, —$C_3H_6$— or —$C_4H_8$—, more preferably —$C_3H_6$— or —$C_4H_8$—, further preferably —$C_3H_6$—.

$Q^4$ and $Q^5$ are each independently preferably —$C_2H_4$—, —$C_3H_6$— or —$C_4H_8$—, more preferably —$C_2H_4$— or —$C_3H_6$—, further preferably —$C_2H_4$—.

$Q^3$ is, for example, preferably a single bond or —O-$Q^6$-, and $Q^6$ is the same as $Q^2$. $Q^3$ is preferably a single bond.

In the following, (meth)acrylates to be used as raw materials for units (A), units (B11), units (B2), units (B3) and units (C) will be exemplified. Here, a (meth)acrylate (B1), a (meth)acrylate (B2) and a (meth)acrylate (B3) will be collectively referred to as a (meth)acrylate (B). In the following description of (meth)acrylates, all symbols have the same meanings as above. Further, —C(=O)O . . . is shown as —COO . . . .

The (meth)acrylate (A) is $CH_2$=CR—COO-$Q^2$-Si($R^7$)$_{3-t}$($OR^8$)$_t$, preferably $CH_2$=CR—COO-$Q^2$—Si($OR^8$)$_3$, particularly preferably $CH_2$=CR—COO—$(CH_2)_3$—Si($OCH_3$)$_3$ or $CH_2$=CR—COO—$(CH_2)_3$—Si($OC_2H_5$)$_3$.

The (meth)acrylate (B11) is $CH_2$=CR—CO-$Q^3$-O—$(CH_2CH_2O)_{n2}$—$R^6$, preferably $CH_2$=CR—COO—$(CH_2CH_2O)_{n2}$—$R^6$ (n2=1 to 300, and $R^6$ is H or $CH_3$). n2 is more preferably from 1 to 20.

The (meth)acrylate (B2) is $CH_2$=CR—COO-$Q^4$-($PO_4^-$)—$(CH_2)_a$—$N^+R^1R^2R^3$, preferably $CH_2$=CR—COO—$(CH_2)_2$—($PO_4^-$)—$(CH_2)_2N^+(CH_3)_3$.

The (meth)acrylate (B3) is $CH_2$=CR—COO-$Q^5$-$N^+R^4R^5$—$(CH_2)_b$—$X^-$, preferably $CH_2$=CR—COO—$(CH_2)_2$—$N^+(CH_3)_2$—$CH_2$—$COO^-$.

The (meth)acrylate (C) is $CH_2$=CR—COO—$R^{10}$, and methyl methacrylate, butyl methacrylate, dodecyl methacrylate, etc. may be mentioned.

The above (meth)acrylate copolymer may, for example, be a copolymer (X21) represented by the following formula (X21).

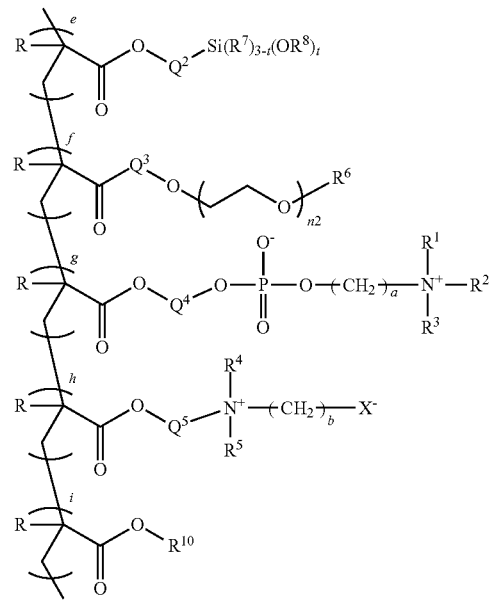

(X21)

Here, in the formula (X21), $R^1$ to $R^6$, $X^-$, and a and b are the same as in the formula 1 to formula 4. $R^1$ to $R^3$ are independently preferably a methyl group, and $R^4$ and $R^5$ are independently preferably a methyl group. $R^6$ is preferably a methyl group or a hydrogen atom. It is preferred that a and b are each independently 2.

n2 is an integer of from 1 to 300, preferably from 1 to 100, more preferably from 1 to 20. $R^7$, $R^8$ and t are the same as in the case of the above formula 5, including preferred embodiments.

R in each unit is independently a hydrogen atom or a methyl group. $R^{10}$ is a hydrogen atom or a monovalent organic group having no biocompatible group and no alkoxysilyl group. $R^{10}$ is preferably a hydrogen atom or a $C_{1-100}$ alkyl group, more preferably a $C_{1-20}$ alkyl group.

The copolymer (X21) may be a random copolymer or a block copolymer.

$Q^2$, $Q^4$ and $Q^5$ are a $C_{2-10}$ divalent hydrocarbon group which may have an etheric oxygen atom between carbon-carbon atoms, wherein a hydrogen atom may be substituted by a halogen atom such as a chlorine atom or a fluorine atom, or a hydroxy group.

$Q^2$ is preferably —$C_2H_4$—, —$C_3H_6$— or —$C_4H_8$—, more preferably —$C_3H_6$— or —$C_4H_8$—, further preferably —$C_3H_6$—.

$Q^4$ and $Q^5$ are each independently preferably —$C_2H_4$—, —$C_3H_6$— or —$C_4H_8$—, more preferably —$C_2H_4$— or —$C_3H_6$—, further preferably —$C_2H_4$—.

$Q^3$ is a single bond or —O-$Q^6$-, and $Q^6$ is the same as $Q^2$. $Q^3$ is preferably a single bond.

In the copolymer (X21), e represents the number of units having an alkoxysilyl group (hereinafter referred to as units (A)) when the total number of units of the copolymer is shown as 100. Similarly, f, g, h and i represent the numbers of units having the structure 1 (4) (hereinafter referred to as units (B1)), units having the structure 2 (hereinafter referred to as units (B2)), units having the structure 3 (hereinafter referred to as units (B3)) and units represented by —(C—C(R)(C(=O)$OR^{10}$))$_i$— (hereinafter referred to as units (C)), respectively, when the total number of units of the copolymer is shown as 100. Hereinafter, —C(=O)O— will be referred to as —COO—.

By adjusting the ratio of e to i in the formula (X21), the contents of the biocompatible group and the alkoxysilyl group (—Si($R^7$)$_{3-f}$(O$R^8$)$_f$) in the copolymer (X21) can be adjusted. The ratio of e to i in the copolymer (X21) is suitably adjusted depending on the solid content composition of the composition (Y). The content of the biocompatible group in the copolymer (X21) is, for example, preferably from 20 to 90% by mass, more preferably from 25 to 83% by mass, further preferably from 30 to 83% by mass, particularly preferably from 40 to 83% by mass. The content of the alkoxysilyl group in the copolymer (X21) is preferably from 1 to 70% by mass, more preferably from 2 to 70% by mass, further preferably from 2 to 25% by mass, particularly preferably from 2 to 15% by mass.

As the copolymer (X21), a copolymer composed solely of units (A) and units (B1) is preferred. Hereinafter, (meth)acrylates which become to be raw materials for units (A), units (B1), units (B2), units (B3) and units (C) will be referred to, respectively, as a (meth)acrylate (A), a (meth)acrylate (B1), a (meth)acrylate (B2), a (meth)acrylate (B3) and a (meth)acrylate (C). Further, a (meth)acrylate (B1), a (meth)acrylate (B2) and a (meth)acrylate (B3) will be collectively referred to as a (meth)acrylate (B). In the following description of the (meth)acrylates, meanings of symbols are all the same as in the copolymer (X21).

The (meth)acrylate (A) is $CH_2$=CR—COO-$Q^2$-Si($R^7$)$_{3-f}$(O$R^8$)$_f$, and $CH_2$=CR—COO-$Q^2$-Si(O$R^8$)$_3$ is preferred, and $CH_2$=CR—COO—($CH_2$)$_3$—Si(O$CH_3$)$_3$ or $CH_2$=CR—COO—($CH_2$)$_3$—Si(O$C_2H_5$)$_3$ is particularly preferred.

The (meth)acrylate (B1) is $CH_2$=CR—CO-$Q^3$-O—($CH_2CH_2$O)$_{n2}$—$R^6$, and $CH_2$=CR—COO—($CH_2CH_2$O)$_{n2}$—$R^6$ (n2=1 to 300, $R^6$ is H or $CH_3$) is preferred. n2 is more preferably from 1 to 20.

The (meth)acrylate (B2) is $CH_2$=CR—COO-$Q^4$-(P$O_4^-$)—($CH_2$)$_a$—$N^+R^1R^2R^3$, and $CH_2$=CR—COO—($CH_2$)$_2$—(P$O_4^-$)—($CH_2$)$_2$—$N^+$($CH_3$)$_3$ is preferred.

The (meth)acrylate (B3) is $CH_2$=CR—COO-$Q^5$-$N^+R^4R^5$—($CH_2$)$_b$—$X^-$, and $CH_2$=CR—COO—($CH_2$)$_2$—$N^+$($CH_3$)$_2$—$CH_2$—COO$^-$ is preferred.

The (meth)acrylate (C) is $CH_2$=CR—COO—$R^{10}$, and methyl methacrylate, butyl methacrylate, dodecyl methacrylate or the like is preferred.

The copolymer (X21) is obtainable, for example, by preparing raw material (meth)acrylates so that e to i become to be in the above-mentioned predetermined ratio, and copolymerizing them by a conventional method such as solution polymerization, bulk polymerization, suspension polymerization, emulsion polymerization or the like in the presence of a polymerization initiator.

Further, in the compound (X2), the content of the structure other than the biocompatible group and the alkoxysilyl group is preferably from 15 to 55% by mass, more preferably from 15 to 40% by mass, from the viewpoint of satisfying both of reduction of the non-specific adsorption amount and water resistance. Mw of the compound (X2) is preferably from 1,000 to 1,000,000, more preferably from 20,000 to 100,000, from the viewpoint of ease of production. Mw of the compound (X2) is calculated by size exclusion chromatography.

The compound (X2) may further be a partially hydrolyzed condensate thereof. When the compound (X2) is a partially hydrolyzed condensate, the degree of condensation is suitably adjusted so as to bring the viscosity to a level not to bring about a problem at the time of forming the surface layer on the surface of the device substrate as described below. From the viewpoint of such viscosity, Mw of the partially hydrolyzed condensate is preferably from 2,000 to 2,000,000, more preferably from 30,000 to 300,000. Also with respect to the following partially hydrolyzed co-condensate, the preferred range of Mw is the same.

The compound (X2) may be a partially hydrolyzed co-condensate obtained by partially hydrolyzing and co-condensing two or more compounds (X2) so as to contain a biocompatible group and an alkoxysilyl group in a desired ratio. The compound (X2) may further be a partially hydrolyzed co-condensate obtained by partially hydrolyzing and co-condensing a compound (X2) and an alkoxysilane compound having no biocompatible group so that the obtainable partially hydrolyzed condensate contains a biocompatible group and an alkoxysilyl group in a desired ratio.

The compound (X3) may, for example, be a (meth)acrylate copolymer obtained by copolymerizing raw material compounds comprising a (meth)acrylate having a biocompatible moiety, a (meth)acrylate having an alkoxysilyl group and a compound capable of introducing a polyoxyethylene chain into the main chain as being essential, and optionally other (meth)acrylates other than these. Here, in this case, since the polyoxyethylene chain as the main chain is not the structure 1 in the structure 4, a (meth)acrylate having the structure 4 is used as the (meth)acrylate having a biocompatible moiety, so that the proportion of the structure 1 in the structure 4 to the total structure 1 in the compound (X3) is adjusted to be at least 50 mol %. Further, as the raw material compounds, the contents of the above-mentioned respective raw material compounds are adjusted so that the obtainable (meth)acrylate copolymer will contain the biocompatible moiety and the alkoxysilyl group in a desired ratio as the compound (X).

In other words, the compound (X3) is preferably a copolymer which comprises units based on a (meth)acrylate having a biocompatible moiety (provided that units based on a (meth)acrylate having the structure 4 is essential), units based on a (meth)acrylate having an alkoxysilyl group and units having a polyoxyethylene chain in the main chain in a predetermined ratio, and optionally units based on other (meth)acrylates other than these.

In the compound (X3), units based on the (meth)acrylate having a biocompatible moiety are preferably the above-mentioned units (B) (provided that units (B11) are essential), more preferably units (B11). As units based on the (meth)acrylate having an alkoxysilyl group, units (A) are preferred. As units having a polyoxyethylene chain in the main chain, units represented by the following formula (B12) are preferred. As units based on other (meth)acrylates, units (C) are preferred.

Formula (B12)

Here, in the formula (B12), $Q^7$ and $Q^8$ are each independently a divalent organic group, and n3 is an integer of from 20 to 200. $Q^7$ and $Q^8$ are preferably a $C_{2-10}$ divalent hydrocarbon group which may have an etheric oxygen atom between carbon-carbon atoms, wherein a hydrogen atom may be substituted by a halogen atom such as a chlorine atom or a fluorine atom, a hydroxy group, or a cyano group.

$Q^7$ and $Q^8$ are preferably —C(CH$_3$)(COOC$_2$H$_5$)—, —C(CH$_3$)(COOCH$_3$)— or —C(CH$_3$)(CN)—, more preferably —C(CH$_3$)(COOCH$_3$)— or —C(CH$_3$)(CN)—, further preferably —C(CH$_3$)(CN)—. n3 is preferably from 40 to 200, more preferably from 40 to 140.

Here, the copolymer (hereinafter referred to also as the copolymer (Z)) having units (B11), units (B12) and units (A) is a copolymer of the present invention which is newly prepared by the present inventors and has not been described in the literature. The copolymer (Z) has the structure 1 in units (B11) and units (B12). The structure 1 in units (B11) is the structure 1 in the structure 4, and the structure 1 in units (B12) is not the structure 1 in the structure 4. Among the copolymers (Z), a copolymer in which the ratio of the structure 1 in the structure 4 to the total structure 1 is adjusted to be at least 50 mol % is in the category of the compound (X3) and can be used for the composition (Y).

In order to adjust the ratio of the structure 1 in the structure 4 to the total structure 1 in the copolymer (Z) to be at least 50 mol %, the amounts of raw material compounds used for the polymerization may be adjusted so that the number of moles of the structure 1 derived from units (B11) becomes larger than the number of moles of the structure 1 derived from units (B12) in the copolymer.

The copolymer (Z) may have optional units such as units (B2), units (B3) and units (C) in addition to units (B11), units (B12) and units (A). As the copolymer (Z), a copolymer (Z1) represented by the following formula (Z1) consisting solely of units (B11), units (B12) and units (A) is preferred.

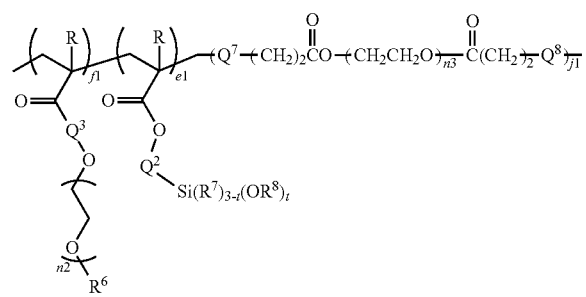

(Z1)

In the formula (Z1), e1 represents the number of units (A) when the total number of units in the copolymer (Z1) is 100. Similarly, f1 and j1 represent the numbers of units (B11) and units (B12), respectively, when the total number of units in the copolymer is 100. The symbols other than e1, f1, and j1 in the formula (Z1) have the same meanings as described above. The copolymer (Z1) may be a random copolymer or a block copolymer.

In a case where the copolymer (Z1) is used as the compound (X3), the ratio of f1 and j1 in formula (Z1) is adjusted so that the requirements for the compound (X3) will be satisfied, that is, to satisfy the relationship of 1>f1/(f1+j1)≥0.5, preferably to satisfy the relationship of 1>f1/(f1+j1)≥0.75.

The content of the biocompatible moiety in the compound (X3) is, for example, preferably from 20 to 90% by mass, more preferably from 25 to 83% by mass, further preferably from 30 to 83% by mass, particularly preferably from 40 to 83% by mass. The content of the alkoxysilyl group in the compound (X3) is preferably from 1 to 70% by mass, more preferably from 2 to 70% by mass, further preferably from 2 to 25% by mass, particularly preferably from 2 to 15% by mass. In a case where the copolymer (Z1) is used as the compound (X3), by adjusting the ratio of e1, f1 and j1, the contents of the biocompatible moiety and the alkoxysilyl group (—Si(R$^7$)$_{3-t}$(OR$^8$)$_t$) in the copolymer (Z1) can be adjusted to be within the above ranges preferable for use as the compound (X3).

The copolymer (Z) is obtainable, for example, by preparing a raw material (meth)acrylate containing a (meth)acrylate (A) and a (meth)acrylate (B11) and a raw material compound which becomes to be units (B12) to be in a predetermined ratio, and copolymerizing them in the presence of a polymerization initiator by a conventional method such as solution polymerization, bulk polymerization, suspension polymerization or emulsion polymerization. At the time of using the copolymer (Z) as the compound (3), the proportions of the respective units, for example, e1, f1 and j1, in the copolymer (Z1), are suitably adjusted.

As the raw material compound which becomes to be units (B12), a compound containing a polyoxyethylene chain and having radically polymerizable groups at both terminals may be mentioned without any particular limitation. Further, the raw material compound which becomes to be units (B12) may be a polymerization initiator containing a polyoxyethylene chain and a radical generating moiety such as an azo group (—N═N—). In the case where the raw material compound which becomes to be units (B12) is a polymerization initiator, such a case is preferred for a reason that a polyoxyethylene chain can be easily introduced into the main chain of the copolymer. As an example of such a polymerization initiator, an azo polymerization initiator having a polyoxyethylene chain may be exemplified. Specifically, a compound represented by the following formula (PI) may be exemplified, and as the compound (PI), VPE-0201 manufactured by Wako Pure Chemical Industries, Ltd. may, for example, be mentioned.

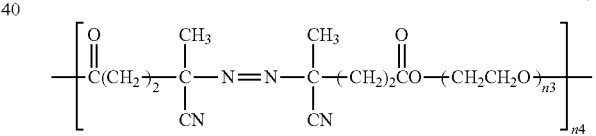

(PI)

In the formula (PI), n3 is the same as n3 in the formula (B12), and n4 is an integer of from 1 to 100. n4 is preferably from 2 to 30, more preferably from 3 to 20.

Further, in the compound (X3), preferably in the compound (X3) composed of the copolymer (Z1), the content of the structure other than the biocompatible moiety and the alkoxysilyl group is preferably from 15 to 55% by mass, more preferably from 15 to 40% by mass, from the viewpoint of satisfying both prevention of the adhesion of algae and water resistance. Mw of the compound (X3) is preferably from 1,000 to 1,000,000, more preferably from 20,000 to 100,000, from the viewpoint of ease of production. Mw of the copolymer (Z1) can be made to be the same as Mw of the compound (X3). Mw of the compound (X3) and the copolymer (Z1) is calculated by size exclusion chromatography.

The compound (X3) may further be a partially hydrolyzed condensate thereof. In a case where the compound (X3) is made to be a partially hydrolyzed condensate, the degree of condensation is suitably adjusted so as to bring the viscosity to a level not to bring about a problem at the time of forming the surface layer on the surface of the water tank body as described below. From the viewpoint of such viscosity, Mw of the partially hydrolyzed condensate is preferably from 2,000 to 2,000,000, more preferably from 30,000 to 300,000. Also with respect to the following partially hydrolyzed co-condensate, the preferred range of Mw is the same.

The compound (X3) may be a partially hydrolyzed co-condensate obtainable by partially hydrolyzing and co-condensing two or more compounds (X3) so as to contain a biocompatible moiety and an alkoxysilyl group in the desired ratio. The compound (X3) may also be a partially hydrolyzed co-condensate obtained by partially hydrolyzing and co-condensing a compound (X3) and an alkoxysilane compound having no biocompatible moiety, so that the obtainable partially hydrolyzed condensate contains a biocompatible moiety and an alkoxysilyl group in the desired ratio as a compound (X).

In the compound (X), the content of the biocompatible group is from 25 to 83% by mass, and the content of the alkoxysilyl group is from 2 to 70% by mass. When the content of the biocompatible group is at least 25% by mass, the obtainable surface layer has the effect of reducing the non-specific adsorption amount. When the content of the biocompatible group is at most 83% by mass, water resistance can be imparted. The content of the biocompatible group in the compound (X) is preferably from 30 to 83% by mass, more preferably from 40 to 83% by mass. Further, when the content of the alkoxysilyl group in the compound (X) is at least 2% by mass, the obtainable surface layer has durability, for example, water resistance. When the content of the alkoxysilyl group is at most 70% by mass, a sufficient amount of the biocompatible group can be introduced. The content of the alkoxysilyl group in the compound (X) is preferably from 2 to 40% by mass, more preferably from 2 to 30% by mass.

As the compound (X), one type may be used alone, or two or more types may be used. In a case where two or more types of the compound (X) are used, it is preferred that two or more types are constituted solely by compounds (X1), or two or more types are constituted solely of compounds (X2). In a case where only the compound (X) is used, the compound (X) is selected so that the content of the biocompatible group and the content of the alkoxysilyl group will be within the above-mentioned predetermined ranges.

The medical device according to the first embodiment of the present invention can be obtained by forming a surface layer by using the above-mentioned compound (X) on the surface of the device substrate in contact with water.

The surface of the device substrate on which the surface layer is to be formed, is as described above. The method for forming the surface layer may be dry coating or wet coating, such as a vacuum deposition method, a CVD method or a sputtering method, and wet coating is preferred.

In a case where formation of the surface layer is conducted by wet coating, the above surface layer can be obtained by using a composition (Y) containing the above compound (X) and a liquid medium. The liquid medium may be one which is capable of uniformly dissolving or dispersing the solid content made of the compound (X), and may be suitably selected from various known liquid media. Since the liquid medium needs to be finally removed at the time of forming the surface layer, its boiling point is preferably in a range of from 60 to 160° C., more preferably from 60 to 120° C.

As the liquid medium, specifically, an alcohol, an ether, a ketone, an ester or the like is preferred. As a liquid medium satisfying the above boiling point condition, specifically isopropyl alcohol, ethanol, propylene glycol monomethyl ether, 2-butanone, ethyl acetate, or the like, may be mentioned. These may be used alone or in combination of two or more of them.

The liquid medium may contain water for the hydrolysis reaction of the compound (X), but it is preferred not to contain water from the viewpoint of storage stability. However, even when the liquid medium does not contain water, the compound (X) can undergo a hydrolysis reaction by water in the atmosphere, and thus, the content of water in the liquid medium is not essential.

The composition (Y) preferably contains the liquid medium in an amount of from 50 to 99.5% by mass, more preferably from 65 to 99% by mass, further preferably from 70 to 99% by mass.

The composition (Y) may contain other components other than the compound (X). Such other components may be solid components other than the compound (X) contained as solid components in the surface layer.

Other solid contents may be components to be cured in the same manner as the compound (X), or may be non-curable components. Such other solid contents may be impurities which have not been completely removed among the raw materials and by-products used in the production process of the compound (X), functional additives, catalysts, etc. Functional additives may be ultraviolet absorbers, light stabilizers, antioxidants, leveling agents, etc.

Further, other solid contents are preferably such solid contents that the obtainable surface layer can satisfy the range of TOC elution amount as described later. Other solid contents are, specifically, preferably components capable of being hydrolytically condensed with the compound (X), and hydrolyzable silyl group-containing components other than the compound (X), and further alkoxysilyl group-containing components are more preferred. With a view to reducing the amount of TOC elution and improving the durability of the effect of reducing the non-specific adsorption amount, the composition (Y) preferably contains no biocompatible group-containing component other than the compound (X), and it is particularly preferred that the composition (Y) contains no solid content other than the compound (X).

As the catalyst, a conventional catalyst used for the hydrolytical condensation reaction of an alkoxysilyl group may be used without particular limitation. Specifically, an acid such as hydrochloric acid, nitric acid, acetic acid, sulfuric acid, phosphoric acid, a sulfonic acid such as methanesulfonic acid or p-toluenesulfonic acid, a base such as sodium hydroxide, potassium hydroxide, ammonia or the like, or an aluminum-based or titanium-based metal catalyst, may be mentioned.

In a case where the compound (X1) is used as the compound (X), as other solid contents, an alkoxysilane compound having no biocompatible group and/or a partially hydrolyzed condensate thereof may be used. As the alkoxysilane compound having no biocompatible group, the above-mentioned compound 6 is preferred. When the alkoxysilane compound having no biocompatible group is made to be a partially hydrolyzed condensate, its Mw is preferably from 100 to 100,000, more preferably from 100 to 10,000.

In a case where the composition (Y) contains the compound (X1) and the alkoxysilane compound having no biocompatible group, as solid contents, in the total of the compound (X1) and the alkoxysilane compound having no biocompatible group, the content of the biocompatible group is preferably from 25 to 83% by mass, and the content of the alkoxysilyl group is preferably from 2 to 70% by mass. That is, it is preferred not to contain a compound having a biocompatible group and/or an alkoxysilyl group other than these, as solid contents. In this case, the proportion of the alkoxysilane compound having no biocompatible group to 100 parts by mass of the compound (X1) is preferably from 50 to 200 parts by mass, more preferably from 50 to 100 parts by mass.

In a case where the compound (X1) is used as the compound (X), in the total solid content, the content in total of other solid contents other than of the compound (X1), the alkoxysilane compound having no biocompatible group and the catalyst, is preferably at most 40% by mass, more preferably at most 20% by mass, most preferably not contained.

Also in a case where the compound (X2) is used as the compound (X), an alkoxysilane compound other than the compound (X2) may be used as the case requires. In the case where the compound (X2) is used as the compound (X), in the total solid content, the content in total of other solid contents other than the compound (X2) and the catalyst is preferably at most 40% by mass, more preferably at most 20% by mass, most preferably not contained.

The solid content concentration in the composition (Y) is preferably from 0.1 to 50% by mass, more preferably from 1 to 30% by mass, further preferably from 1 to 15% by mass. When the solid content concentration is within the above range, the thickness of the surface layer formed by wet coating using the composition (Y) tends to be easily within such a range that the effect of reducing the non-specific adsorption amount and its durability can be sufficiently exhibited. The solid content concentration of the composition (Y) can be calculated from the mass of the composition (Y) after vacuum drying at 80° C. for 3 hours and the mass of the composition (Y) before heating. It may also be calculated from the total solid content and the amount of the liquid medium that are blended at the time of the production of the composition (Y).

The method for producing the composition (Y) is not particularly limited. The compound (X), other solid contents and the liquid medium may be mixed so as to have the above contents. In the composition (Y), as described above, the content of the biocompatible group in the compound (X) is from 25 to 83% by mass, and the content of the alkoxysilyl group is from 2 to 70% by mass. Therefore, the surface layer made of a cured product formed on the surface of the device substrate using the composition (Y) has a reduced non-specific adsorption amount and is excellent in durability, particularly in water resistance.

As a method of forming a surface layer by wet coating, a method may be mentioned which comprises applying a composition (Y) containing the above liquid medium to a predetermined surface of a device substrate to obtain a coating film (hereinafter referred to also as "coating step"), and curing the coating film to obtain a surface layer (hereinafter referred to also as "curing step").

The method for applying the composition (Y) to the surface of the device substrate in the coating step may, for example, be a dip coating method, a spin coating method, a wipe coating method, a spray coating method, a squeegee coating method, a die coating method, an inkjet method, a flow coating method, a roll coating method, a casting method, a Langmuir-Blodgett method, a gravure coating method, etc.

As a method for curing the coating film in the curing step, heating is preferred. The heating temperature depends on the type of the alkoxysilyl group-containing component containing the compound (X), but is preferably from 50 to 150° C., more preferably 100 to 150° C. Further, in the curing step, removal of the liquid medium is usually carried out at the same time. Therefore, the heating temperature is preferably a temperature of at least the boiling point of the liquid medium. However, in a case where heating and drying are difficult due to e.g. the material of the device substrate, removal of the liquid medium is carried out by avoiding the heating.

In the formation of the surface layer by wet coating, a processing treatment other than the coating step and the drying step may be included, as the case requires. For example, in a case where the composition (Y) does not contain water, a treatment such as humidification may be performed at the same time as the curing step or before or after the curing step.

Further, after the formation of the surface layer, excess compounds that are compounds in the surface layer may be removed as the case requires. A specific method may, for example, be a method of pouring a solvent, for example, a compound used as a liquid medium for the composition (Y), to the surface layer, or a method of wiping off with a cloth impregnated with a solvent, for example, a compound used as a liquid medium for the composition (Y).

The thickness of the surface layer is preferably from 10 to 100,000 nm, particularly preferably from 10 to 10,000 nm. When the thickness of the surface layer is at least the lower limit value in the above range, a sufficient effect of reducing the non-specific adsorption amount, and its durability, particularly water resistance, tend to be easily exhibited. When the thickness of the surface layer is at most the upper limit value in the above range, the strength will be excellent. The thickness of the surface layer is obtained by measurement by an X-ray reflectivity measuring device represented by ATX-G manufactured by Rigaku Corporation.

When the surface layer is immersed in water at 40° C. for 7 days, the elution amount of total organic carbon (TOC: Total Organic Carbon) per unit area of 1 $cm^2$ of the surface layer (hereinafter referred to also as the "TOC elution amount") is preferably at most 10 mg/L. In other words, the TOC elution amount is the mass [mg] of TOC eluted in water when the surface layer of an area of 1 $cm^2$ is immersed in 1 L of water at 40° C. for 7 days. If constituent components are eluted from the surface layer, such may present an influence on e.g. the analysis of biological substances using the medical device, and therefore, the TOC elution amount is more preferably at most 1 mg/L, further preferably at most 0.5 mg/L, particularly preferably at most 0.3 mg/L.

TOC is one showing the total amount of organic matter by the amount of carbon. In this specification, the surface layer TOC elution amount can be measured specifically as follows. The TOC concentration [mg/L] in the treated water after immersing the surface layer in a predetermined amount of water at 40° C. for 7 days, is measured. The water used for immersion shall be distilled water or ion-exchanged water. By dividing the TOC concentration obtained as described above by the area (unit: $cm^2$) of the immersed surface layer, the TOC elution amount [mg/L] can be obtained. The measurement of the TOC concentration in water can be carried out by a common TOC meter, for example, TNC-6000 (manufactured by Toray Engineering Co., Ltd.).

As a test sample of the surface layer to be used for measuring the TOC elution amount, a surface layer simple substance obtained by preparing a surface layer on a releasable substrate and peeling it, may be used, or a surface layer-attached substrate may be used in which a surface layer is formed on a substrate having a TOC elution amount of 0 [mg/L] under the above conditions (at 40° C. for 7 days).

The medical device targeted by the present invention is a device to be used for medical treatment such as treatment, diagnosis, anatomy or biological examination, and includes any device that is inserted into or brought into contact with a living body such as a human body or that is in contact with a medium (such as blood) taken out from the living body. Specific examples of the medical device include medicines, quasi drugs, medical instruments, etc. The medical instruments are not particularly limited, and include cell culture containers, cell culture sheets, vials, plastic-coated vials, syringes, plastic-coated syringes, ampoules, plastic-coated ampoules, cartridges, bottles, plastic-coated bottles, pouches, pumps, sprayers, stoppers, plungers, caps, lids, needles, stents, catheters, implants, contact lenses, microchannel chips, drug delivery system materials, artificial blood vessels, artificial organs, hemodialysis membranes, guard wires, blood filters, blood preservation packs, endoscopes, biochips, sugar chain synthesizing equipment, molding aids, packaging materials, etc.

Since the medical device of the present invention has the surface layer made of a cured product of the compound having the biocompatible group and the alkoxysilyl group as described above, the non-specific adsorption amount is reduced, and at the same time, its durability is excellent, whereby eluents from the surface layer will be reduced. Therefore, for example, even when used as a detection device such as a microchannel chip or a biochip for a long period of time, it is possible to maintain excellent detection accuracy.

EXAMPLES

In the following, the present invention will be described in detail with reference to Examples. However, the present invention is not limited by the following description. "%" means "% by mass" unless otherwise specified. Ex. 1 to 6 and Ex. 13 to 14 are Examples of the present invention, and Ex. 7 to 12 are Comparative Examples.

(Synthesis and Preparation of Compound (X))
<Compound (X1)>

Compounds classified into compound (X1) and compounds having no biocompatible group for Comparative Examples were prepared as follows.

Compound (X11-1): As compound (X11-1) having the structure shown below, that is, 2-[methoxy(polyoxyethylene)$_{9-12}$propyl]trimethoxysilane, a commercially available product, SIM6492.72 (trade name, manufactured by Gelest), was prepared. The compound (X11-1) is a compound in which the terminal hydrogen atom of the compound (X11) is substituted by a methyl group, n1 is from 9 to 12, $Q^1$ is —$C_3H_6$—, t is 3, and $R^8$ is a methyl group.

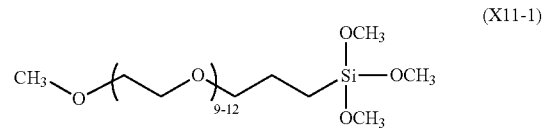

Compound (X11-2): As compound (X11-2) having the same molecular structure as compound (X11-1) except that the number of repeating oxyethylene groups is from 6 to 9, that is, 2-[methoxy(polyethyleneoxy)$_{6-9}$ propyl]trimethoxysilane, a commercially available product, SIM6492.7 (trade name, manufactured by Gelest), was prepared.

Compound (X12-1): Compound (X12-1) having the structure shown below is the same as compound (X12) in which n1 is from 7 to 8, $Q^1$ is —$CONHC_3H_6$—, t is 3, and $R^8$ is ethyl, and was synthesized by the following method.

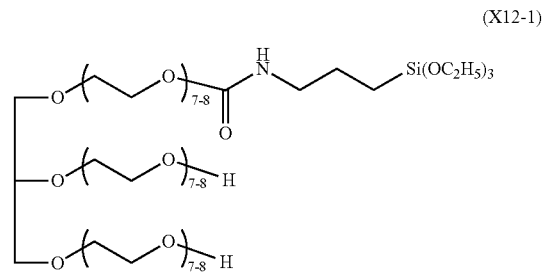

In a 300 mL eggplant-shaped flask, 263 g (259 mmol) of polyoxyethylene glyceryl ether wherein n1 is 7 to 8 (indicated as "polyoxyethylene polyol A" in Table 1) and 64.1 g (259 mmol) of KBE-9007 (manufactured by Shin-Etsu Silicone Co., Ltd., product name, Triethoxysilylpropyl isocyanate) were added. Subsequently, to the obtained mixture, 3.27 g (32.4 mmol) of triethylamine in an amount of 1% by mass was added, and then the mixture was stirred at 80° C. for 16 hours. Then, the obtained reaction mixture was heated and decompressed by a rotary evaporator to remove triethylamine to obtain compound (X12-1) as a colorless transparent liquid. The obtained amount was 327 g, and the yield was 100%.

Compound (Cf1): As compound (Cf1), (3-methoxypropyl)trimethoxysilane ($CH_3$—O—$(CH_2)_3$—$Si(OCH_3)_3$), commercial product, SIM6493.0 (trade name, manufactured by Gelest), was prepared.

The type of polyoxyethylene polyol used in the synthesis of compound (X12-1) and the addition amount (equivalent amount) of KBE-9007 to polyoxyethylene polyol, and in each of the above compounds, Mw, the repeating number (n1) of ($CH_2CH_2O$) in group 1 (4)), the proportion (mol %) of group 1 being group 1 in group 4, the proportion (% by mass) of the biocompatible group (group 1 (4)) in the compound, and the proportion (% by mass) of the alkoxysilyl group, are shown in Table 1.

TABLE 1

| | | Compound abbreviation | | | |
|---|---|---|---|---|---|
| | | (X11-1) | (X11-2) | (X12-1) | (Cf1) |
| Reaction conditions | Type of polyoxyethylene polyol Amount (equivalent) of KBE-9007 to polyoxyethylene polyol | Commercial product | Commercial product | A 1 | Commercial product |

TABLE 1-continued

| | | | Compound abbreviation | | | |
|---|---|---|---|---|---|---|
| | | | (X11-1) | (X11-2) | (X12-1) | (Cf1) |
| Properties of compound | Mw | | 590 | 459 | 1260 | 194.3 |
| | n1 | | 9-12 | 6-9 | 7-8 | 0 |
| | Proportion of structure 4 | Mol % | 100 | 100 | 67 | 0 |
| | Proportion of biocompatible group | % by mass | 69.8 | 61.1 | 77.0 | 0 |
| | Proportion of alkoxysilyl group | % by mass | 20.5 | 26.4 | 12.9 | 62.4 |
| Mw after partially hydrolyzed condensation | | | — | — | 2730 | 700 |

<Monomer Abbreviations>
(1) Monomer (A)
  KBM-503: manufactured by Shin-Etsu Silicone Co., Ltd., product name, trimethoxysilylpropyl methacrylate ($CH_2$=$C(CH_3)$—COO—$(CH_2)_3$—$Si(OCH_3)_3$)
  KBM-5103: manufactured by Shin-Etsu Silicone Co., Ltd., product name, trimethoxysilylpropyl acrylate ($CH_2$=CH—COO—$(CH_2)_3$—$Si(OCH_3)_3$)
(2) Monomer (B1)
  AME-400: Blemmer AME-400 (manufactured by NOF CORPORATION, trade name, $CH_2$=CH—COO—$(CH_2CH_2O)_9$—$CH_3$)
  HEMA: $CH_2$=$C(CH_3)$—COO—$CH_2CH_2O$—H
  HEA: $CH_2$=CH—COO—$CH_2CH_2O$—H Production Example 1

In a 500 mL three-necked flask, 57.0 g (438 mmol) of HEMA, 3.00 g (12.1 mmol) of KBM-503, 119 g of 1-methoxy-2-propanol, 21 g of diacetone alcohol, and 600 mg (2.61 mmol) of dimethyl 2,2'-azobis (2-methylpropionate) were added. The monomer concentration in the reaction solution was 30% by mass, and the initiator concentration was 1% by mass. Then, the obtained mixture was stirred at 75° C. under a nitrogen atmosphere for 16 hours and air-cooled to room temperature to obtain a colorless transparent liquid (solution containing 30% by mass of copolymer (X21-1)). The obtained amount was 200 g, and the yield was 100%.

Production Examples 2 to 4

Copolymers (X21-2) and (X21-3) were produced in the same manner as in Production Example 1 except that the monomer composition was changed as shown in Table 2. Also, a homopolymer (M) of a monomer having a biocompatible group was produced.

In the compounds (copolymers) obtained in Production Examples 1 to 4, Mw, the repeating number (n2) of ($CH_2CH_2O$) in the group 1 (4), the proportion (% by mass) of the biocompatible group (group 1 (4)) and the proportion (% by mass) of the alkoxysilyl group are shown in Table 2.

Production Example 5

In a 500 mL three-necked flask, 8.85 g (30.0 mmol) of 2-methacryloyloxyethylphosphorylcholine (manufactured by Tokyo Chemical Industry Co., Ltd.) and 9.94 g (70.0 mmol) of butyl methacrylate (manufactured by Tokyo Chemical Industry Co., Ltd.) were dissolved in 43.6 g of ethanol. Then, 0.18 g (1.14 mmol) of 2,2-azobisisobutyronitrile (manufactured by Wako Pure Chemical Industries, Ltd.) was added as a polymerization initiator. The monomer concentration in the reaction solution was made to be 30% by mass, and the initiator concentration was made to be 1% by mass. Then, the obtained mixture was stirred at 75° C. under a nitrogen atmosphere for 16 hours, and air-cooled to room temperature, whereupon the reaction solution was added dropwise to diethyl ether, and the precipitate was collected to obtain a white solid polymer (2-methacryloyloxyethylphosphorylcholine/butyl methacrylate (MPC/BMA) copolymer).

TABLE 2

| | | | Properties of compound | | | | |
|---|---|---|---|---|---|---|---|
| Production Example | Compound (copolymer) abbreviation | Monomer composition (mass ratio) | Mw | n2 | Proportion of biocompatible group (% by mass) | Proportion of alkoxysilyl group (% by mass) | Mw after partially hydrolyzed condensation |
| 1 | (X21-1) | HEMA/KBM-503 = 95/5 | 43200 | 1 | 43.8 | 2.4 | 93600 |
| 2 | (X21-2) | HEA/KBM-5103 = 95/5 | 38500 | 1 | 49.1 | 2.6 | 71400 |
| 3 | (X21-3) | AME-400/KBM-5103 = 95/5 | 65200 | 9 | 82.9 | 2.6 | 135000 |
| 4 | (M) | HEMA = 100 | 41000 | 1 | 46.1 | 0 | — |

Ex. 1

By vacuum vapor depositing compound (X11-1) on the surface of a washed glass plate having a length of 23 mm, a width of 25 mm and a thickness of 3 mm (manufactured by Asahi Glass Co., Ltd., trade name: FL3, transparent float soda lime glass) (back pressure: $3.4 \times 10^{-4}$ Pa, substrate temperature: 25° C.), a surface layer having a film thickness of 2 nm was formed to obtain a glass plate provided with a surface layer.

Ex. 2

A glass plate provided with a surface layer was obtained in the same manner as in Ex. 1, except that compound (X11-2) was used in place of compound (X11-1).

Ex. 3

A solution (solid content concentration: 30% by mass) containing copolymer (X21-1) was added to a solvent having 1-methoxy-2-propanol, diacetone alcohol and a 0.1% by mass of nitric acid aqueous solution mixed in a mass ratio of 51:9:40, so that the solid concentration would be 10% by mass and stirred at 50° C. for 16 hours, to obtain a liquid composition containing a partially hydrolyzed condensate of copolymer (X21-1). Mw of the obtained partially hydrolyzed condensate is shown in Table 2. Further, this liquid composition was dissolved in a mixed solvent of methoxypropanol and diacetone alcohol at a ratio of 85:15 (mass ratio) so that the solid content concentration became 1.0% by mass, to obtain a composition for forming a surface layer.

On the surface of the same glass plate as in Ex. 1, by a dip coating method using the composition for forming a surface layer obtained as described above, a coating film of the composition for forming a surface layer was formed. Then, this was dried in a hot air circulation oven at 150° C. for 1 hour to form a surface layer with a film thickness of 1.8 nm, to obtain a glass plate provided with the surface layer.

Ex. 4, 5 and 6

A glass plate provided with a surface layer was obtained in the same manner as in Ex. 3, except that copolymer (X21-1) was changed to copolymer (X21-2), copolymer (X21-3) or compound (X12-1). Mw of the partially hydrolyzed condensate of copolymer (X21-2), copolymer (X21-3) or compound (X12-1) is shown in Table 2 or Table 1.

Ex. 7

Homopolymer (M) was dissolved in a mixed solvent of methoxypropanol and diacetone alcohol at a ratio of 85:15 (mass ratio) so that the solid content concentration became to be 1.0% by mass, to obtain a composition for forming a surface layer. Using the obtained composition for forming a surface layer, a glass plate provided with a surface layer was obtained in the same manner as in Ex. 3.

Ex. 8

A glass plate provided with a surface layer was obtained in the same manner as in Ex. 3, except that compound (Cf1) was used instead of copolymer (X21-1). Mw of the partially hydrolyzed condensate of compound (Cf1) is shown in Table 1.

Ex. 9

A glass plate similar to that in Ex. 1 was left to stand at room temperature for 16 hours in an albumin (BSA, manufactured by Sigma-Aldrich) solution diluted to 1.0 mg/mL by a phosphate buffer, to obtain a glass plate provided with a surface layer.

Ex. 10

The MPC/BMA copolymer obtained in Production Example 5 was dissolved in ethanol so that the solid content concentration became to be 10% by mass to obtain a coating liquid. A glass plate similar to that in Ex. 1 was coated with the obtained coating liquid by a dip method and left to stand at 25° C. for 15 minutes, thereby to obtain the glass plate provided with a surface layer.

Ex. 11

To a 50 mL vial bottle, 0.16 g of KBM-503 (manufactured by Shin-Etsu Chemical Co., Ltd.), 2.88 g of methanol and 0.96 g of an aqueous acetic acid solution adjusted to pH3 in advance were added and stirred at room temperature for 2 hours for hydrolysis. Thereafter, 12.0 g of isopropyl alcohol was further added to prepare a coating liquid. A glass plate similar to that in Ex. 1 was coated with the coating liquid obtained in this Ex. by a dip method, left to stand at 25° C. for 15 minutes and then cured at 120° C. for 1 hour, to obtain the glass plate provided with a coating layer.

Ex. 13 and 14

(Production of Copolymer (Z1))

As copolymer (Z1) satisfying the requirements of compound (3), copolymer (X3-1) and copolymer (X3-2) were produced as follows.

(Copolymer (X3-1))

In a 500 mL three-necked flask, 45.0 g (346 mmol) of HEMA, 3.00 g (12.1 mmol) of KBM-503, 119 g of 1-methoxy-2-propanol, 21 g of diacetone alcohol and 12 g of VPE-0201 (manufactured by Wako Pure Chemical Industries, Ltd.) as a polymerization initiator (5.4 mmol as an azo group) were added. Subsequently, the obtained mixture was stirred at 80° C. under a nitrogen atmosphere for 16 hours and air-cooled to room temperature to obtain a colorless transparent liquid (a solution containing 30% by mass of copolymer (X3-1) which is copolymer (X3-Z1) represented by the following formula (X3-Z1) in which f1 is 95, e1 is 3, and j1 is 2). The obtained amount was 200 g, and the yield was 100%.

Using the obtained colorless transparent liquid, a liquid composition containing a partially hydrolyzed condensate of copolymer (X3-1) was obtained in the same manner as in Ex. 3. The liquid composition was directly used as composition 13 for forming a surface layer.

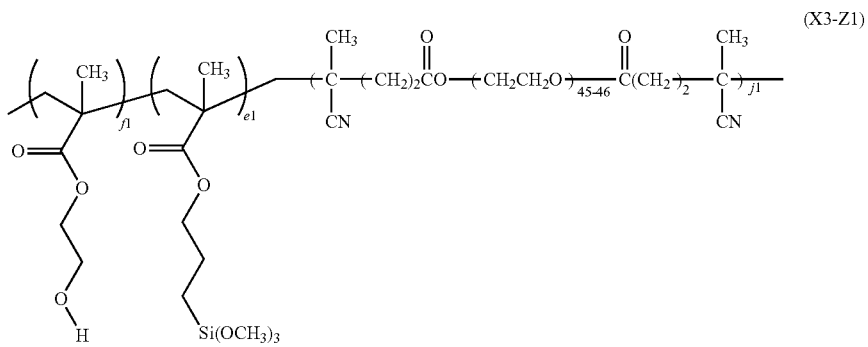

(X3-Z1)

In copolymer (X3-1), Mw is 28500, Mw of the obtained partially hydrolyzed condensate is 52100, in the structure 1, the proportion of the structure 1 in the structure 4 is 98 mol %, and the proportion of the biocompatible moiety (structure 1) is 52.3% by mass, and the proportion of the alkoxysilyl group is 2.4% by mass.

(Copolymer (X3-2))

In the same manner as in the production of the above copolymer (X3-1), except that the mass of HEMA was changed to 42.0 g and the mass of KBM-503 was changed to 6.0 g, copolymer (X3-2) being copolymer (X3-Z1) in which f1 is 91, e1 is 7, and j1 is 2, was produced as a colorless transparent liquid (a solution containing 30% by mass of copolymer (X3-2)). The obtained amount was 200 g, and the yield was 100%. Using the obtained colorless transparent liquid, in the same manner as in Ex. 3, a liquid composition containing a partially hydrolyzed condensate of copolymer (X3-2) was obtained. The liquid composition was used as it was, as composition 14 for forming a surface layer.

In copolymer (X3-2), Mw is 29600, Mw of the obtained partial hydrolyzed condensate is 54600, in the structure 1, the proportion of the structure 1 in the structure 4 is 98 mol %, and the proportion of the biocompatible moiety (structure 1) is 50.0% by mass, and the proportion of the alkoxysilyl group is 4.9% by mass.

(Production of Glass Plates 13 and 14 Provided with Surface Layer)

Using each of the obtained compositions 13 and 14 for forming a surface layer, a glass plate provided with a surface layer was obtained in the same procedure as in Ex. 3.

Acrylamide (manufactured by Tokyo Chemical Industry Co., Ltd.) adjusted to 3% by mass with ethanol was applied on the glass plate provided with a coating layer obtained as described above, by a dip method and heated at 110° C. to polymerize the acrylamide thereby to obtain a glass plate provided with a surface layer.

(Cell Non-Adhesiveness)

Each of the glass plates provided with a surface layer in the respective Ex. and the glass plate (Ex. 12) having no surface layer, was placed in a glass vial of 50 cc, and 10 cc of IPA was further added thereto, followed by washing with ultrasonic waves for 10 minutes. After suctioning IPA, ethanol was similarly put in an amount of 10 cc, followed by washing with ultrasonic waves for 10 minutes and then by drying to prepare a substrate for evaluation.

The washed 23 mm×25 mm substrate for evaluation thus obtained was placed in a 35 mmφ polystyrene Petri dish (1000-035: manufactured by ATG Techno glass Co., Ltd.), and UV irradiation sterilization was performed for 16 hours on a clean bench.

A cell suspension was prepared by using, as a culturing medium, MEM having 10% FBS added, so that TIG-3 cells confirmed to have a cell survival rate of at least 97% at the time of seeding would be 130,000 cells per 3 mL. The cells were seeded by dispensing 3 mL of the cell suspension into the Petri dish in which the above-mentioned substrate for evaluation was placed, and cultured in an incubator at 37° C. for 24 hours. Thereafter, an observation area was set to be a range of 1.8 mm×1.3 mm, and in three observation areas, microscopic observation (10 magnifications) was carried out, whereby judgement of the adhesion was conducted based on the presence or absence of extension of cells according to the following standards. A state in which cells are spread in an elliptical or perfect circle shape on the substrate for evaluation is defined as extension of cells.

"○": Cells are not attached to the observation areas at all locations.

"Δ": In at least one observation area, cells are attached to a part thereof.

"X": Cells are attached to almost the entire observation areas at all locations.

(Measurement of Elution Amount)

Each of the glass plates provided with a surface layer in the respective Ex. obtained as described above, or the glass plate having no surface layer in Ex. 12, was placed in a 100 mL glass vial together with 6.4 mL of distilled water, and left to stand still at 40° C. for 7 days to let TOC be eluted. The TOC concentration [mg/L] of the obtained eluate was measured by a TOC meter TNC-6000 (manufactured by Toray Engineering Co., Ltd.) and divided by the area (5.75 cm$^2$) of the above test sample to calculate the TOC elution amount [mg/L] per unit area of 1 cm$^2$ of the surface layer. Since the TOC elution amount from the glass plate is 0 mg/L, the obtained TOC elution amount means the TOC elution amount from the surface layer.

(Durability of Cell Non-Adhesiveness)

The glass plate after the above measurement of the elution amount was taken out from the distilled water, and the cell non-adhesiveness was evaluated in the same manner as described above.

TABLE 3

| | Abbreviation or identification of surface layer | Cell non-dhesiveness (130,000 cells) Initial | Cell non-dhesiveness (130,000 cells) After water resistance test | TOC elution amount [mg/L] |
|---|---|---|---|---|
| Ex. 1 | (X11-1) | ○ | ○ | 0 |
| Ex. 2 | (X11-2) | ○ | ○ | 0 |
| Ex. 3 | (X21-1) | ○ | ○ | 8 |
| Ex. 4 | (X21-2) | ○ | ○ | 0 |
| Ex. 5 | (X21-3) | Δ | Δ | 5 |
| Ex. 6 | (X12-1) | ○ | Δ | 4 |
| Ex. 7 | (M) | ○ | × | 12 |
| Ex. 8 | (Cf1) | × | × | 0 |
| Ex. 9 | BSA | ○ | × | 100> |
| Ex. 10 | MPC/BMA copolymer | ○ | × | 100> |
| Ex. 11 | Cured layer obtained by polymerizing trimethoxysilylpropyl methacrylate and acrylamide | ○ | Δ | 50 |
| Ex. 12 | Nil | × | × | 0 |
| Ex. 13 | (X3-1) | ○ | ○ | 0 |
| Ex. 14 | (X3-2) | ○ | ○ | 0 |

From Table 3, it is evident that the glass plates having a surface layer formed, in Examples of the present invention (Ex. 1 to 6 and Ex. 13 to 14) are excellent in cell non-adhesiveness and have the non-specific adsorption amount reduced, as compared with the glass plates having a surface layer formed, in Comparative Examples (Ex. 8 to 12). Further, it is also evident that durability of the non-specific adsorption is excellent, and the TOC elution amount is small.

This application is a continuation of PCT Application No. PCT/JP2019/007931, filed on Feb. 28, 2019, which is based upon and claims the benefit of priority from Japanese Patent Application No. 2018-075271 filed on Apr. 10, 2018. The contents of those applications are incorporated herein by reference in their entireties.

What is claimed is:

1. A medical device, comprising:
a device substrate; and
a surface layer formed on at least part of a surface of the device substrate and configured to be in contact with water,
wherein the at least part of the surface of the device substrate on which the surface layer is provided includes an inorganic material, the surface layer includes a cured product of a compound having a biocompatible group and an alkoxysilyl group, the biocompatible group comprises at least one type selected from the group consisting of a structure of formula 1, a structure of formula 2 and a structure of formula 3:

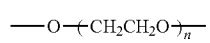

Formula 1

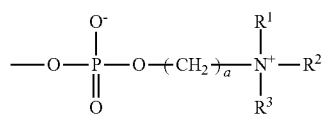

Formula 2

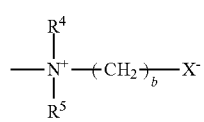

Formula 3 wherein:
in the formula 1, n is an integer of from 1 to 300, from 50 to 100 mol % in the structure of the formula 1 is a structure of formula 4, n in the formula 4 is an integer of from 1 to 300, $R^6$ is a hydrogen atom or a $C_{1-5}$ alkyl group, and units of (B12) are present;

Formula (B12)

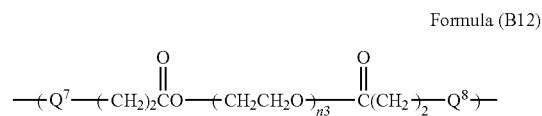

provided that in the formula (B12), $Q^7$ and $Q^8$ are each independently a divalent organic group, and n3 is an integer of from 20 to 200;
in the formula 2, $R^1$ to $R^3$ are each independently a $C_{1-5}$ alkyl group, and a is an integer of from 1 to 5; and
in the formula 3, $R^4$ and $R^5$ are each independently a $C_{1-5}$ alkyl group, $X^-$ is a group of formula 3-1 or a group of formula 3-2, and b is an integer of from 1 to 5,

Formula 4

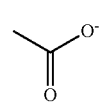

Formula 3-1

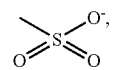

Formula 3-2 the compound is a copolymer having
units based on a (meth)acrylate having the structure of the formula 1 provided that from 50 to 100 mol % in the structure of the formula 1 is the structure of the formula 4,
units based on a (meth)acrylate having an alkoxysilyl group having formula 5,

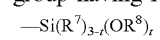  Formula 5, where $R^7$ is a $C_{1-18}$ alkyl group, $R^8$ is a $C_{1-18}$ alkyl group, and t is an integer of from 1 to 3, and the units of the formula (B12), wherein
the content of the biocompatible group in the compound, which is the mass of formula 1+formula 2+formula 3, not including the mass of any group $R^6$ of formula 4, is from 25 to 83% by mass, and
the content of the alkoxysilyl group is from 2 to 70% by mass.

2. The medical device according to claim 1, wherein when the surface layer is immersed in water at 40° C. for 7 days, the elution amount of total organic carbon (TOC) to water per unit area of 1 cm$^2$ of the surface layer is at most 10 mg/L.

3. The medical device according to claim 1, wherein the above compound is such a compound that in a polyoxyethylene polyol or a polyoxyethylene alkyl ether (wherein the alkyl has from 1 to 5 carbon atoms) having at least one hydroxy group, an alkoxysilyl group is introduced via a hydroxy group and a linking group which the polyoxyethylene polyol or the polyoxyethylene alkyl ether has.

4. The medical device according to claim 1, wherein the above compound is such a compound that in a polyoxyethylene polyol or a polyoxyethylene polyol alkyl ether (wherein the alkyl has from 1 to 5 carbon atoms) having at least one hydroxy group, an alkoxysilyl group is introduced so as to be bonded via an oxygen atom derived from the hydroxy group, or via a linking group having an oxygen atom derived from the hydroxy group bonded with —(CH$_2$)$_k$—, —CONH(CH$_2$)$_k$—, —(CF$_2$)$_k$—, —CO(CH$_2$)$_k$—, —CH$_2$CH(—OH)CH$_2$O(CH$_2$)$_k$— (k represents an integer of from 2 to 4), —CH$_2$OC$_3$H$_6$— or —CF$_2$OCH$_6$—.

5. The medical device according to claim 1, wherein the above compound is a copolymer having units based on a (meth)acrylate having a structure represented by the above formula 1 (provided that from 50 to 100 mol % is the structure represented by the formula 1 in the structure represented by the above formula 4), and units based on a (meth)acrylate having an alkoxysilyl group.

6. The medical device according to claim 1, wherein the above compound comprises a copolymer having units based on a (meth)acrylate having a structure represented by the above formula 1 and units based on a (meth)acrylate having an alkoxysilyl group, and a polymer consisting only of units based on a (meth)acrylate having a structure represented by the above formula 1, and from 50 to 100 mol % in the structure represented by the above formula 1 contained in the solid content of the above compound has a structure represented the formula 1 in the structure represented by the above formula 4.

7. The medical device according to claim 1, wherein the above compound is a copolymer having units represented by the following formula (A), units represented by the following formula (B11) and units represented by the following formula (B12),

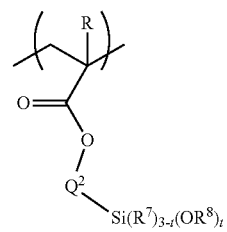

Formula (A)

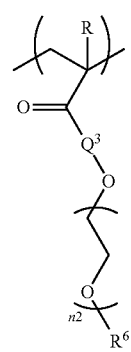

Formula (B11)

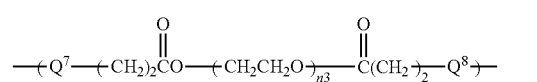

Formula (B12)

provided that the symbols in the formula (A), the formula (B11) and the formula (B12) are as follows;
in the formula (A) and the formula (B11), R is a hydrogen atom or a methyl group;
in the formula (A), $Q^2$ is a divalent organic group, $R^7$ and $R^8$ are each independently a $C_{1-18}$ alkyl group, t is an integer of from 1 to 3, and when $R^7$ and $OR^8$ are present in a plurality, the respective $R^7$ and $R^8$ may be the same or different;
in the formula (B11), $Q^3$ is a single bond or a divalent organic group, n2 is an integer of from 1 to 300, and $R^6$ is a hydrogen atom or a $C_{1-5}$ alkyl group;
in the formula (B12), $Q^7$ and $Q^8$ are each independently a divalent organic group, and n3 is an integer of from 20 to 200.

8. The medical device according to claim 1, wherein the above device substrate is made of glass.

* * * * *